United States Patent
Silber et al.

(10) Patent No.: US 7,351,584 B2
(45) Date of Patent: Apr. 1, 2008

(54) HEPATOCYTE BIOREACTOR SYSTEM FOR LONG TERM CULTURE OF FUNCTIONAL HEPATOCYTE SPHEROIDS

(75) Inventors: Paul M. Silber, Ellicott City, MD (US); Nancy L. Cowger, Catonsville, MD (US); Ana P. Miller, Annapolis, MD (US); Lanika A. Brown, Hyattsville, MD (US); Albert P. Li, Columbia, MD (US)

(73) Assignee: In Vitro Technologies, Inc., Baltimore, MD (US)

( * ) Notice: Subject to any disclaimer, the term of this patent is extended or adjusted under 35 U.S.C. 154(b) by 221 days.

(21) Appl. No.: 10/505,785

(22) PCT Filed: Feb. 26, 2003

(86) PCT No.: PCT/US03/05638

§ 371 (c)(1),
(2), (4) Date: Aug. 26, 2004

(87) PCT Pub. No.: WO03/072764

PCT Pub. Date: Sep. 4, 2003

(65) Prior Publication Data

US 2005/0084965 A1 Apr. 21, 2005

(51) Int. Cl.
*C12N 5/08* (2006.01)
(52) U.S. Cl. .................. 435/383; 435/370; 435/375; 424/93.7
(58) Field of Classification Search ........... 435/325, 435/370, 373, 383, 384
See application file for complete search history.

(56) References Cited

U.S. PATENT DOCUMENTS 5,624,839 A 4/1997 Yada et al.

OTHER PUBLICATIONS

Li, et al., *A Simplified Method for the Culturing of Primary Adult Rat and Human Hepatocytes as Multicellular Spheroids*, In Vitro Cell. Dev. Biol., 28A:673-677, Sep.-Oct. 1992.
Battle, et al., *Progressive Maturation Resistance to Microcystin-LR Cytotoxicity in Two Different Hepatospheroidal Models*, Cell Biology and Toxicology, 1999, pp. 3-12.
Clejan, et al., *Effects of Simulated Microgravity on DU 145 Human Prostate Carcinoma Cells*, Biotechnology and Bioengineering, vol. 50, 1996, pp. 587-597.
Dabos, et al., *The Simulated Microgravity Environment Maintains Key Metabolic Functions and Promotes Aggregation of Primary Porcine Hepatocytes*, Biochimica et Biophysica Acta 1526 (2001) pp. 119-130.
*Notification of Transmittal of the International Search Report or the Declaration; International Search Report*, Jun. 30, 2003, pp. 1-7.

*Primary Examiner*—Ruth A Davis
(74) *Attorney, Agent, or Firm*—Loeb & Loeb, LLP

(57) ABSTRACT

A rotating wall vessel is used as a culture vessel and bioreactor for the cultivation of hepatocytes in the form of spheroids to generate a culture with many properties of the intact liver. These properties include enzyme activity comparable to fresh cells and long-term maintenance of viability and cellular function for periods on the order of months. The cultures may be used to produce hepatocyte products, evaluate metabolism of an agent, propagate Hepatitis C virus and test agents as inhibitors of this virus. Thus, the culture system disclosed herein makes long term functional cultivation of human hepatocytes feasible.

11 Claims, 4 Drawing Sheets

HEPATOCYTE BIOREACTOR SYSTEM FOR LONG TERM CULTURE OF FUNCTIONAL HEPATOCYTE SPHEROIDS

BACKGROUND OF THE INVENTION

1. Field of the Invention

The present invention in the field of biology provides a novel method and culture system for long term culture of functional hepatocytes by first preparing hepatocyte spheroids and inoculating these into a specialized bioreactor that is a rotating wall vessel wherein the cells are cultured under conditions that promote three-dimensional aggregation and cellular differentiation.

2. Description of the Background Art

Hepatocyte Spheroids

Landry, J. et al., *J. Cell Biol.* 101: 914-923 (1985) described the spontaneous formation of spheroidal aggregates when primary rat liver cells were incubated on a nonadherent plastic dish. Three distinct cell morphologies were noted: surface monolayer cells; hepatocytes grouped as islands with deposition of extracellular matrix components; and structures resembling bile ducts. Tong, J Z, et al., *Exp. Cell Res.* 189:87-92 (1990), studied multicellular spheroids formed from newborn rat liver cells and detected secretion of liver proteins, specifically albumin and transferrin, for up to 60 days when the culture medium was supplemented with dexamethasone, glucagon, insulin, and epidermal growth factor. These investigators (Tong, J Z, et al., *Exp. Cell Res.* 200:326-332 (1992)) also observed maintenance of liver-specific functions in spheroid cultures of adult rat hepatocytes, demonstrating metabolism of lidocaine by the cytochrome P450 (CYP) enzyme 3A2, for up to 14 days. CYP 1A1 was strongly induced by methylcholanthrene, remaining constant for up to 22 days.

Interestingly, the presence of serum factors inhibited spheroid formation under certain conditions (Koide, N. et al., *Exp. Cell Res.* 186:227-235 (1990)).

One of the present inventors and his colleagues (A. P. Li et al., *In Vitro Cell. Dev. Biol.* 28A:673-677 (1992a)) was the first to report spheroid formation by human hepatocytes. Their simple, yet proven, method involved seeding $5 \times 10^6$ hepatocytes in culture medium on a 100-mm plastic dish and shaking at 50 rpm overnight. This method caused 90% of the cells to aggregate in the form of spheroids, which were shown to possess many of the morphological characteristics of intact liver.

U.S. Pat. No. 5,624,839 disclosed that lipid-bound glycosaminoglycan promoted spheroid formation.

Cytochrome P450s (CYPs)

CYPs are a family of enzymes, localized to the cytoplasmic side of the endoplasmic reticulum of the liver cell, that catalyze the oxidation of organic compounds, resulting in increased water solubility which promotes excretion from the cell. CYPs are obviously important for processing xenobiotics. Table 2 lists a number of CYP enzymes in rat liver that are responsible for metabolism (and detoxification) of a number of drugs.

Once hepatocytes are isolated from the liver and are grown in conventional primary cultures, the activity of these important enzymes is rapidly lost. This loss is particularly prominent for rat hepatocytes which lose 80% of their CYP activity in the first 24 hours of culture (Paine, A J, In: Berry, Minn. et al. (eds.), *The Hepatocyte Review*, Kluwer Academic Publishers, Netherlands, pp. 411-420, 2000).

Rotating Wall Culture Vessels

Rotating wall vessels or RWVs are a class of bioreactors developed by and for NASA beginning in about 1990 that were designed to grow suspension cultures of animal cells in a quiescent environment that simulates microgravity. RWVs were first described in a number of U.S. patents (U.S. Pat. Nos. 5,026,650; 5,153,131; 5,153,133) assigned to NASA, and thereafter in several additional patents (U.S. Pat. Nos. 5,437,998; 5,665,594; 5,702,941) assigned to Synthecon, Inc., who served as a contractor and licensee of NASA Other patents describe the same principle as the RWV, i.e., horizontal rotation for mixing or suspending cells in culture medium. With the exception of Ingram et al. (U.S. Pat. No. 5,523,228), however, these patents do not disclose the culture of freely suspended cells. For example, in Rhodes et al. (U.S. Pat. No. 5,104,802), cells are confined inside a hollow fiber rotating with the culture vessel. U.S. Pat. No. 6,117,674 described a process for propagating a pathogen in a three-dimensional tissue mass in RWV culture. The foregoing patents are all incorporated by reference in their entirety.

During operation, an RWV is completely filled with medium and rotates about a horizontal axis. Oxygenation occurs in a bubble-free manner via a silicone rubber membrane that covers the back wall of the cultivation chamber. Cells are evenly distributed and semi-buoyant during cultivation, and mixing is accomplished without stirring by end-over-end rotation of the vessel (Schwarz, R P, et al., *J. Tiss. Cult. Meth.* 14:51-58, 1992; Cowger, N L, et al., *Biotechnol. Bioeng* 64:14-26, 1999).

RWVs have proven beneficial to the cultivation of many cell types for tissue engineering applications. Unlike conventional vessels, a RWV accommodates three-dimensional (3D) assembly and co-location of dissimilar cell types in a gently mixed environment. The result is more extensive 3D growth with increased cell-cell and cell-matrix interactions and cellular differentiation that more closely resembles organized living tissue (Spaulding, G F, et al., *J. Cell. Biochem.* 51:249-251, 1993). These properties of RWVs have been exploited to grow and study primary cells from various normal tissues (Goodwin, T J, et al., *Proc. Soc. Exp. Biol. Med.* 202:181-192, 1993; Freed, LE et al., *In Vitro Cell. Dev. Biol.* 33:381-385, 1997) and cells from tumors. For example, aggregates of human prostate tumor cells were more differentiated in terms of their growth, morphology, and cytoskeletal protein expression when cultured in a RWV compared to "control" tumor cells grown in conventional spinner flasks or static cultures (Clejan, S. et al, *Biotechnol. Bioeng.* 50:587-597, 1996). Khaoustov, VI, et al., *In Vitro Cell. Dev. Biol.* 35:501-509. 1999) described the culture of human hepatocytes in an RWV, primarily providing morphological descriptions, though this document disclosed continuous albumin secretion and urea nitrogen production over a period of 20 days.

Of the existing patent disclosures describing functional hepatocytes in vitro, with utility as "artificial livers," none describe or suggest the use of freely suspended cells in a rotating bioreactor. For example, Li et al. (U.S. Pat. No. 5,270,192) disclosed a hepatocyte bioreactor in which hepatocytes or aggregates are entrapped inside a matrix of glass beads. In connection with hepatocyte spheroid formation, U.S. Pat. No. 5,624,839 (noted above) disclosed a composition that promoted this process.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

The present invention is directed to the use of a rotating wall vessel (RWV) for the cultivation of hepatocytes in the form of spheroids to generate cultures that maintain many important properties of intact liver. These properties include long-term viability and maintenance of cellular function for periods on the order of months, and enzyme activities comparable to fresh cells. The type of RWV in the present invention is termed a High Aspect Ratio Vessel ("HARV") which is depicted in the patent cited above and in other related publications. See also, Cowger and O'Connor, 1997, "Application of simulated microgravity to insect-cell culture," In: Maramorosch, K et al. (eds), *Invertebrate Cell Culture, Novel Directions and Biotechnology Applications*, Science Publishers, Enfield, N.H., p. 131-138, hereby incorporated by reference.

The present invention is directed to a method for cultivation of mammalian hepatocytes in a viable functional state for a prolonged period, preferably at least about 7-30 days, which comprises the steps of:
(a) culturing a single cell suspension of mammalian hepatocytes for a period of between about 12 and about 168 hours, preferably between about 24 and 72 hours in a flat surface-containing culture vessel under conditions that permit aggregation of hepatocytes into spheroids comprising viable cells;
(b) obtaining the spheroids and introducing them into a rotating wall vessel culture chamber where the spheroids remain in suspension during subsequent culture with rotation;
(c) incubating the vessels under conditions of rotation such that the spheroids remain in suspension and the hepatocytes remain viable and capable of metabolizing drugs or toxins via enzymes of the cytochrome P450 system, which drugs or toxins are ones that are normally metabolized by hepatocytes in vivo.

Pre-aggregation may be performed in any culture vessel where adherence to the vessel surface is inhibited or discouraged. Vessels coated with materials such as polymethacrylate or poly-L-lysine that inhibit electrostatic or other interactions that cause cells to adhere may be used. Any form of stirring or mixing, including conventional spinner cultures, may be used at this stage, as long as the conditions promote aggregation and spheroid formation.

The source of primary hepatocytes may be any of a number of mammalian species, preferably human, but also rat, mouse, pig, rabbit, or nonhuman primate.

The methods disclosed herein for culture and testing of hepatocytes can also be used with other cell types, particularly cells that do not thrive or function adequately without pre-attachment to other cells or to solid supports. Such cells include primary mammalian cells that do not originate in the liver, and various types of stem or progenitor cells.

The culture medium in the present invention can be any basal medium, or combination thereof, that supports hepatocyte viability, including Waymouth MB 752/1; Williams' Medium E; Eagle's MEM; Dulbecco's MEM/Ham's F12; RPMI 1640; or Leibovitz L-15. Preferably, the medium contains supplements that help maintain hepatocyte morphology and differentiated function. These supplements can be conveniently categorized as: (1) growth factors, such as epidermal growth factor (EGF); (2) hormones, preferably peptide hormones such as insulin and glucagon; and (3) glucocorticoids, such as dexamethasone and hydrocortisone.

Any of the known RWVs can be used herein, although a preferred RWV is a HARV.

In another embodiment, this invention provides a method for evaluating the metabolism of an agent that is metabolized by mammalian liver cells in vivo, comprising
(a) culturing mammalian hepatocytes as described above;
(b) adding the agent being evaluated to the hepatocyte culture in the culture vessels for a period of time sufficient for enzymes of the hepatocytes to metabolize the agent and converting it to one of more metabolites thereof;
(c) identifying the presence of, or measuring the concentration of, the one or more metabolites in the medium or cells of the culture, thereby evaluating the metabolism of the agent.

Also included is a method for producing a product, preferably a biomolecule such as a liver protein, e.g., albumin, that is made by, and, optionally, secreted by, normal mammalian hepatocytes in vivo, comprising
(a) culturing mammalian hepatocytes as described above, optionally in the presence of an agent that induces synthesis and/or secretion of the product, for a period of time sufficient to stimulate the synthesis and/or secretion of the molecule;
(b) obtaining the product from the medium or cells of the culture, thereby producing the product.

Also provided is a method for cultivation of mammalian hepatocytes in a viable functional state, which comprises inoculating a HARV with pre-aggregated hepatocytes or nascent hepatocyte spheroids, in a culture medium and incubating the hepatocytes and under conditions wherein hepatocytes are viable and metabolically active for a period of at least about 4 days, preferably at least about 7 days, more preferably at least about 14 days, even more preferably at least about 30 days.

In another embodiment, the present invention is directed to a method for propagating Hepatitis C virus (HCV) in cultured hepatocytes, comprising:
(a) culturing primate hepatocytes as described above;
(b) inoculating the cultured hepatocytes with an inoculum of HCV, for example serum from an HCV infected subject, and permitting the virus to infect, replicate in and be released from the hepatocytes;
(c) harvesting the medium of the culture which contains the HCV, thereby growing HCV.

The above method may further comprise the step (d) enriching or isolating the HCV from the medium.

The amount or titer of HCV present in the harvested medium or in the enriched or isolated preparation may be measured, preferably using one or more of the following criteria: (i) presence of HCV negative-strand RNA; (ii) presence of HCV positive-strand RNA; (iii) transmission of infection to cells of a fresh hepatocyte culture by transfer of the medium or enriched/isolated viral preparation; and (iv) infection of chimpanzees by intravenous inoculation of the medium or isolated/enriched virus, preferably at a dose of at least about $10^4$ $CID_{50}$.

Also provided herein is a method for testing an agent for its activity as an inhibitor of HCV replication or propagation in hepatocytes, comprising:
(a) culturing primate, preferably human, hepatocytes in accordance with claim 1;
(b) inoculating the cultured hepatocytes with an inoculum of HCV and permitting the virus to infect, replicate in and be released from the hepatocytes;

(c) before, during or after step (b), adding to the virus-infected cultures the agent being tested for inhibitory activity, (d) to a parallel culture or set of cultures of hepatocytes infected with HCV as in steps (a) and (b), adding negative control agent that does not inhibit HCV replication or propagation (e) harvesting the medium of the cultures of (c) and (d); and (f) measuring the amount or titer of HCV present in the harvested medium, wherein a lower amount or titer of virus in the cultures of (c) compared to the cultures of (d) is indicative that the agent is an inhibitor.

The foregoing method may further include the use of a positive control group in which an agent or combination of agents known to inhibit HCV replication or propagation is added to a parallel culture or set of cultures. The amount or titer of resulting virus in the presence of the positive control inhibitor or inhibitors should be significantly less than the amount in the cultures of (d) above, thereby indicating that the virus replication or propagation in the cultures is inhibitable by the positive control agent. The amount of virus in the test group (c) may be higher than, similar to or lower than the positive control, depending on the inhibitory potency of the test agent.

DESCRIPTION OF THE PREFERRED EMBODIMENTS

Following their discovery that single cells suspensions of hepatocytes do not survive or function adequately following their inoculation into any of a number of culture vessels or systems, including RWVs, the present inventors discovered that pre-aggregation of the hepatocytes for a period of between about 24 hours and 7 days in culture dishes before transfer to the RWV permits the hepatocytes to survive and function as normal liver cells for prolonged periods. This approach and culture system permits many practical uses of these long term cultures that have heretofore not been possible, as described below.

It was initially believed that certain advantages accompanied the use of fresh hepatocytes as a single cell suspension to inoculate the RWV. These advantages included saving time and effort compared to "pre-aggregation" (see below) and the potential for a steady maintenance of enzyme activity. However, experiments conducted with single cells showed the rapid loss of viability after several hours in either of two types of RWVs, which may be related to inadequate oxygen tension. In petri dishes, $pO_2$ is stable at 130 to 140 mm Hg. In contrast, in the RWV, the $pO_2$ of oxygen-saturated medium falls rapidly following inoculation to less than 60 mm Hg.

Hepatocyte spheroids (discussed in more detail below) survive and function well in the HARV bioreactor but not in the Slow-Turning Lateral Vessel (STLV), also known as a Cylindrical Cell Culture Vessel. The HARV is designed with a larger ratio of gas-exchange surface area-to-volume and thus oxygenates more efficiently than the STLV.

Other factors likely contribute to the fate of single cells inoculated into the RWV. The addition of serum to the medium shows potential to improve the outcome. Higher production of three metabolites of dextromethorphan were observed when single-cell rat hepatocytes were cultured in medium supplemented with 2% serum. Metabolite production was enhanced by 40-70% in the presence of serum. After 24 hours, hepatocytes cultured as cells in serum-free medium were nonviable whereas, in the same cultures with serum, approximately 50% of the cells formed aggregates and remained viable.

In view of the foregoing disadvantages of single cell hepatocyte suspensions, the present inventors conceived of, and demonstrated that pre-aggregation of hepatocytes into spheroids before adding them to the HARV bioreactor resulted in the sought-after characteristics of long-term hepatocyte cultures, characterized primarily by prolonged cell viability of the culture and normal hepatocyte function. Such longevity of viability and differentiated function may be any period of time exceeding that which was previously known for hepatocytes, e.g., at least about 4 days, preferably at least about 7 days, more preferably at least about 14 days or even more than 30 days.

Figure 1:
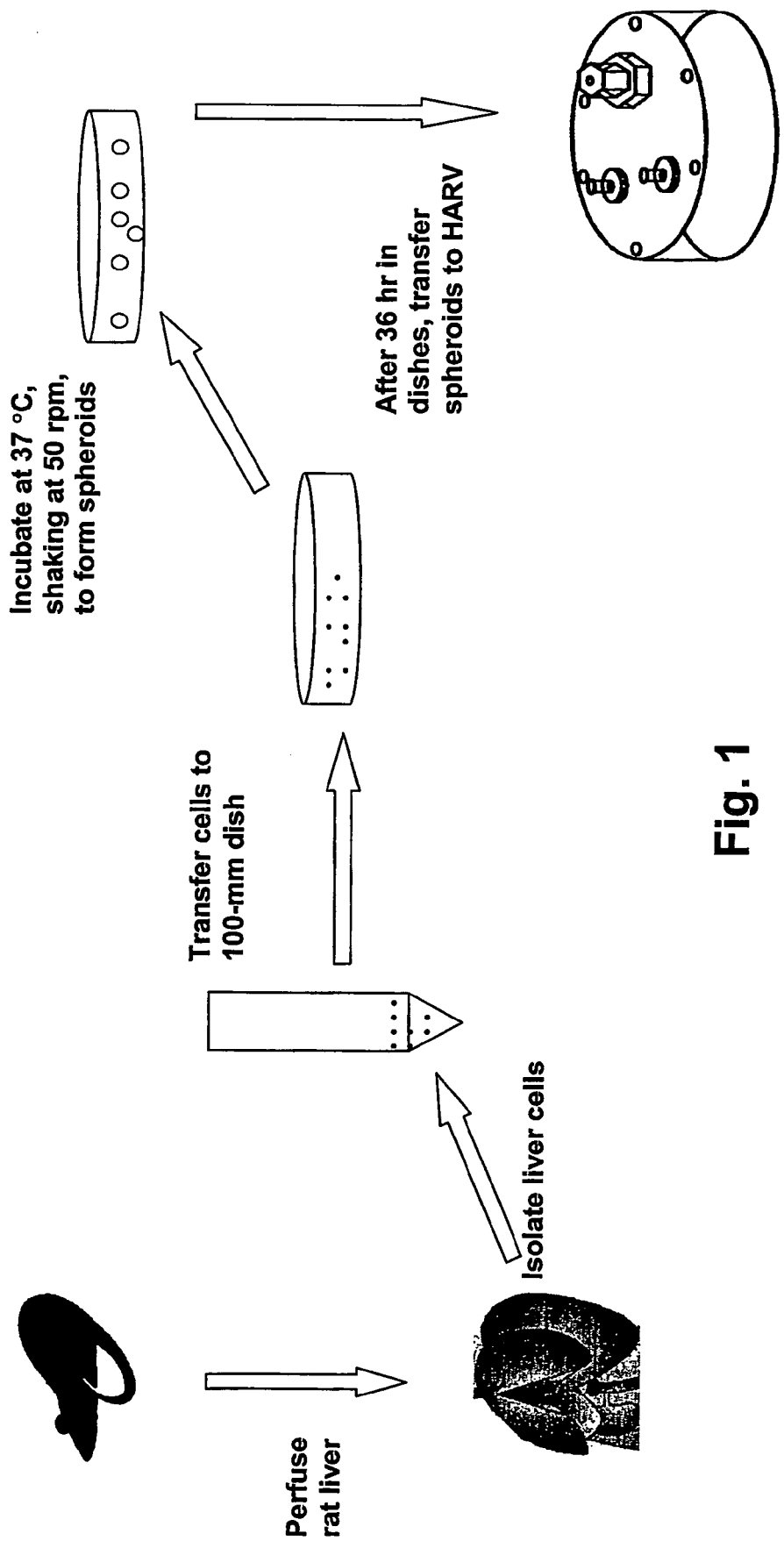
FIG. 1 is a schematic representation of the novel method for processing primary hepatocytes and preparing spheroids for inoculation into the HARV bioreactor.

Thus, the present invention comprises inoculating a HARV with pre-aggregated hepatocytes or nascent spheroids. The procedure for preparing the spheroids is described in more detailed below and depicted schematically in FIG. 1. Use of pre-aggregated hepatocytes in such a bioreactor results not only in successful cultures, but cultures possessing many advantages over other culture types that were known in the art.

The present bioreactor and culture system has many uses, some of which are listed and discussed below.

Pathogen Infectivity Studies

Hepatitis C is an important pathogen for which no vaccine is yet available. There is no reliable in vitro method for culturing hepatitis viruses—and an urgent need in the art for such a capability for the development of new therapeutics. The present long term hepatocyte culture will permit cultivation of Hepatitis C virus.

Studies of Long-Term Liver Toxicity of Drugs

There is a need for a convenient and reliable laboratory tool to study liver toxicity of any new drug under development or to evaluate agents which are considered to have chronic liver toxicity such as those whose effects are manifest only over long periods of exposure in vivo. The present hepatocyte culture system is ideally suited for such studies, as illustrated by the present Examples showing metabolite formation in vitro.

Mass Production of Secreted Liver Biomolecules, Particularly Proteins and Lipids.

Commercial production of biomolecules from hepatocytes is enabled by the bioreactor and culture system of the present invention. Albumin production is exemplified below. The present invention is especially advantageous for production of liver-derived compositions that have been difficult to obtain by other means. The present system is ideal for production of bioactive metabolites from prodrugs. Thus, a prodrug type of compound may be added to the present RWV hepatocyte cultures for large scale production of its active metabolite which may be difficult to prepare economically by conventional chemical synthesis. It is believed that scale-up to larger volume cultures can be accomplished by those of ordinary skill in the art without undue experimentation.

Isolation of Hepatocytes

Hepatocytes are isolated from perfused liver using well-established methods, e.g., Li et al., 1992b, *J. Tissue Culture Meth.* 14:139-146). Likewise, the procedure for preparing hepatocyte aggregates or spheroids has been published by Li et al., 1992a, supra and is outlined in FIG. 1.

In the present inventors' laboratory, rat hepatocytes cells are commonly derived from male Sprague-Dawley rats weighing 225-250 g. Porcine, monkey or ape hepatocytes as well as human hepatocytes, which are prepared from donor livers obtained from accident victims or other recently deceased donors in whom liver function is believed to be normal, are prepared in a similar manner, though volumes are adjusted accordingly.

In the "pre-aggregation" or "spheroid-formation" stage of culture, the isolated hepatocytes are cultured in 100-mm diameter sterile petri dishes, or an equivalent thereof, with 10 mL of Waymouth's 752/1 medium, pH 7.28, or an equivalent thereof. Medium is preferably supplemented with the following: 2.24 g/L sodium bicarbonate, 2.38 g/L HEPES buffer, 11.2 mg/L alanine, 12.8 mg/L serine, 24 mg/L asparagine, 0.3 mL heptanoic acid, 5 mg/L linoleic acid, 0.175 mg/L aminolevulinic acid, 5 mg/L insulin, 5 mg/L transferrin, 5 μg/L selenous acid, 39.2 μg/L dexamethasone, 0.25 mg/L amphotericin B, 84 mg/L gentamicin sulfate, 84 mg/L amikacin sulfate, 100 U/mL penicillin G sodium, and 100 mg/L streptomycin sulfate. Those of ordinary skill in the art will know how to select these additives and manipulate their concentrations to achieve the objectives of this invention with ordinary experimentation that is not undue.

Any conditions that prevent cell adherence to the bottom of the dish (or other surface of alternate vessels) are preferred during this stage. Although cell concentration is typically about $10^6$ cells/mL, and $0.5-1 \times 10^6$ is preferred, a broader range of concentrations may be used, for example, between about $10^4$ and $10^8$ cells/mL, as long as the selected concentration permits and preferably promotes, spheroid formation.

The preferred bioreactor is a RWV such as the 10-mL HARV produced by Synthecon, Inc. (Houston, Tex.), filled with medium of the above composition (or equivalent) and containing about $5 \times 10^7$ pre-aggregated rat hepatocytes, though a broader range of cell concentrations may be used. Various drugs or other substrates may be added to the bioreactor and the metabolites collected for analysis of hepatocyte activity as is exemplified below. In a typical HARV, the bottom member of the vessel is composed of a paraformaldehyde-based plastic, in a preferred embodiment, Delrin® (or another tough plastic such as that used for molded articles, gears, etc.). A silicone rubber membrane is fixed onto its surface with silicone sealant. On the vessel's top member, composed of a plastic polymer such as poly (4,4'-isopropylidine diphenylcarbonate or poly(4,4'-carbonato-2,2'-diphenylpropane (in one embodiment, Lexan®), are two stainless-steel syringe ports for sampling and feeding. A larger filling port with a cap is present on preferred larger HARVs, but not on the 10-mL model. When the vessel's two members are bolted together, a chamber is formed—commonly having a 10-mL culture volume that is to be completely filled with medium during operation. All vessel parts are autoclavable.

As for the rotator base unit, for operation, the vessel is mounted on the motor shaft. An air pump delivers filtered air to the back of the vessel where gas exchange occurs across the silicone membrane.

Below is an exemplary and preferred procedure for preparing the bioreactor for use, adding substrate, and collecting metabolites. It is understood by those of skill in the art the procedures and reagents described below may be modified by the user in accordance with conventional procedures and knowledge in the art of cell culture and drug metabolism. For example, if using a larger HARV, volumes, cell numbers, reagent concentrations, times, etc., may be subject to a range of modifications without materially changing the nature of the present invention.

Basic Startup Procedure

1. Autoclave a 10-mL HARV according to the manufacturer's instructions, with peripheral screws loosened and foil covering the syringe ports.
2. Assemble the vessel inside a sterile hood. Using an Allen wrench, tighten the six peripheral screws. Remove the foil covering the two syringe ports and install a sterile one-way stopcock valve onto each. Set the vessel aside.
3. Obtain the cells to be inoculated in the form of hepatocyte spheroids prepared in flat surface culture vessels, preferably 100 mm petri dishes, from the incubator and transfer to the sterile hood.
4. Remove 8 to 9 mL of medium from each dish using a pipet. Cells may be concentrated from the pre-aggregation cultures by gravity sedimentation (at 1×g) or velocity sedimentation. Simple centrifugation to concentrate the cells is preferably avoided.
5. Remove the cells from several (typically 5 to 10) dishes using a single 10-nL syringe. Attach the syringe onto one of the HARV ports and inoculate the cells into the vessel. Commonly, about $5 \times 10^7$ cells are added to each 10-mL HARV. During inoculation of the HARV, it is important that the aggregates/spheroids be handled gently with minimization of shear forces.
6. Discard the inoculation syringe. Fill a new 10-mL syringe with medium, and attach it to one valve port. Add medium to the vessel until nearly full while manipulating air bubbles underneath the second open port.
7. To remove remaining air bubbles, attach a 5-mL syringe to the other port and position the vessel so that the bubbles move directly under that port. Push on the 10-mL inoculating syringe to force the bubbles to escape via the other port and into the 5 mL syringe.
8. Once the bubbles have been removed, close the valve, remove and discard the 5-mL syringe, but leave the 10-mL syringe, with some medium remaining, attached.
9. Wipe the open port with, e.g., an alcohol or other antiseptic pad, and attach an end cap.
10. The vessel can now be placed onto its rotator base inside a 37° C. incubator having a 5% $CO_2$ atmosphere. The vessel is typically rotated at a speed of approximately 29 rpm. The precise speed is optional and is governed by the need to maintain the spheroids in gentle suspension. As aggregates increase in size over time, the rotational speed may be increased manually.

Modified Procedure for Adding Substrate

Following Step 6, above:

7A. Remove the one-way stopcock valve from the empty syringe port, keeping it sterile.

8A. Add the desired substrate using a micropipettor with sterile tip. Preferably, add no more than 1% (v/v) of any nonaqueous solvent with the substrate. Insert the micropipettor tip directly inside the HARV syringe port and add the substrate to the vessel contents. Place the one-way stopcock back onto this port.

9A. Attach a 5-mL syringe onto this valve port and remove the 10-mL syringe from the other side, keeping it sterile. With the 5-mL syringe, gently remove 25 to 50% of the medium, keeping the cells relatively undisturbed. Then, gently push these contents back into the vessel. This step insures that the contents are well mixed. Note that a modified mixing method may be equally effective.

10A. Re-attach the 10-mL syringe. Use the 5-mL syringe to withdraw an initial sample of about. 0.5 mL, replacing that volume with fresh medium from the 10-mL syringe. Store the initial sample frozen until ready to analyze (e.g., by HPLC).

11A. From this point, follow steps 7 through 10 above.

Collecting Metabolites from the Bioreactor

1. Remove the HARV from its rotating base. Dispose of any extra medium in the attached 10-mL syringe.
2. Using a 10-mL syringe, remove contents (medium plus cells) from the vessel and place into a conical centrifuge tube. At this point, cell viability can be determined using a small sample of the cells.
3. Add an equal volume of "stopping" solution to the conical tube and mix. The "stopping" solution may be (i) methanol, (ii) a 1:1 methanol/0.1 M Tris acetate mixture, or some other solvent, depending on the properties of a particular substrate.
4. Add 5 mL of "stopping" solution to the HARV and mix it around to contact all surfaces. Withdraw this solution and save it separately as the extraction sample. This step is included to increase yield of substrate and/or metabolites, as some compounds have become adsorbed to the vessel surfaces.
5. With the vessel contents mixed with solvent from step 3, centrifuge at 1000 rpm (250×g) or any gravitational force that pellets the cells without disrupting them, e.g, from about 150-400×g, for approximately 5 minutes.
6. Transfer samples of the supernatant to HPLC vials or, alternatively, store frozen until analysis time. The concentrations of substrate and metabolites derived from HPLC analysis must be corrected for dilution by the solvent in step 3.
7. The cell pellet from step 5 should be processed to (1) recover the intracellular fraction of metabolite and (2) analyze total protein. Resuspend the cell pellet in 0.1 M Tris acetate. Homogenize on ice. To an aliquot of this homogenate, add an equal volume of "stopping" solution. Place briefly on ice and then centrifuge. Sample the supernatant and analyze for metabolite by HPLC. The remaining cell homogenate may be stored frozen until a convenient time to perform protein analysis.

Modified Procedure for Collection of Metabolites from Continuous Bioreactor Culture The above procedure describes harvest of the entire contents of the bioreactor. For continuous production of a secreted metabolite, the procedure may be modified to harvest only a fraction of the bioreactor contents. The same cell culture may then be maintained for an extended period and medium sampled repeatedly to test metabolite levels. The procedure is essentially as detailed below for changing medium in the RWV. Up to 75% of the conditioned medium may be conveniently removed and replaced with fresh medium. The conditioned medium may be processed by immediate freezing, adding solvent, etc., depending on the characteristics of the metabolite of interest and the chosen method for purification and analysis of the metabolite.

Changing Medium in RWV

The following procedure should be performed on the first day following startup and every 2 to 6 days afterwards, preferably about every third day.

1. Remove the vessel from rotator base and transfer to a sterile hood.
2. Discard the medium in the attached 10-mL syringe. Reattach this syringe to the valve port. Remove the cap from the second valve port, placing it aside on a sterile alcohol pad, and open the valve.
3. Tilt the vessel slightly to allow the cells to settle away from both syringe ports. Aggregates settle quickly.
4. Pull gently on the 10-mL syringe to remove approximately 25 to 75% of conditioned medium from the vessel (about 2.5 to 7.5 mL). During this removal process, the vessel position will need to be adjusted slightly in order to keep the syringe port in contact with the medium. Discard the syringe and its contents or save supernatant sample for any desired measurements.
5. Fill a new 10-mL syringe with medium. Attach this to the syringe port, and gently push fresh medium into the vessel except for the last 2 to 3 mL remaining in the syringe.
6. Attach a 5-mL syringe to the second valve port. Maneuver the vessel so that air bubbles are positioned directly underneath this port. Push on the 10-mL syringe to allow bubbles to escape into the 5-mL syringe.
7. Close the valve before removing the 5-mL syringe. Swab this port with an alcohol pad and recap it. Wipe any media spills from the surface of the vessel with an alcohol pad. The 10-mL syringe stays on the vessel with the valve open. Place the vessel back on its rotator base inside the 37° C. incubator.

Having now generally described the invention, the same will be more readily understood through reference to the following examples which are provided by way of illustration, and are not intended to be limiting of the present invention, unless specified.

EXAMPLE I

Cell Viability and Morphology

Figure 2A:
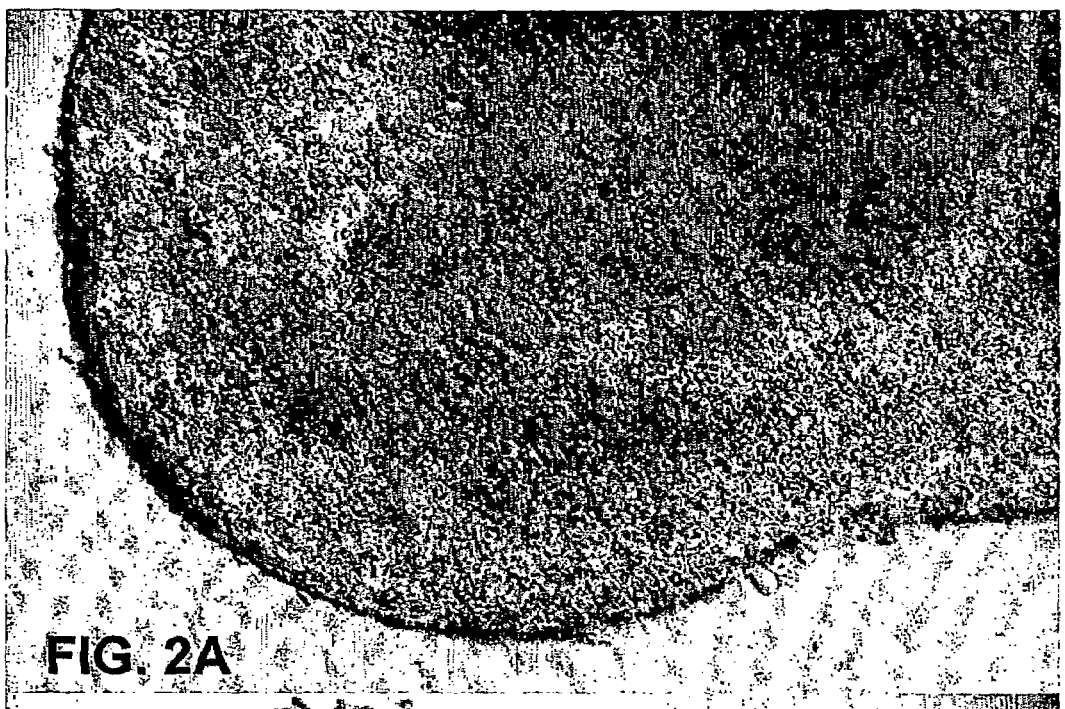
FIGS. 2A and 2B show large viable aggregates composed of multiple hepatocytes in HARV cultures at day 11 (FIG. 2A) and day 16 (FIG. 2B) using the method of the invention. Very few cells in these aggregates stain with trypan blue (seen as black coloring in these grayscale photographs), indicating high viability. The overall color of these spheroid aggregates ranges from tan to dark brown, as would be expected from a large mass of viable liver cells.
Figure 2B:
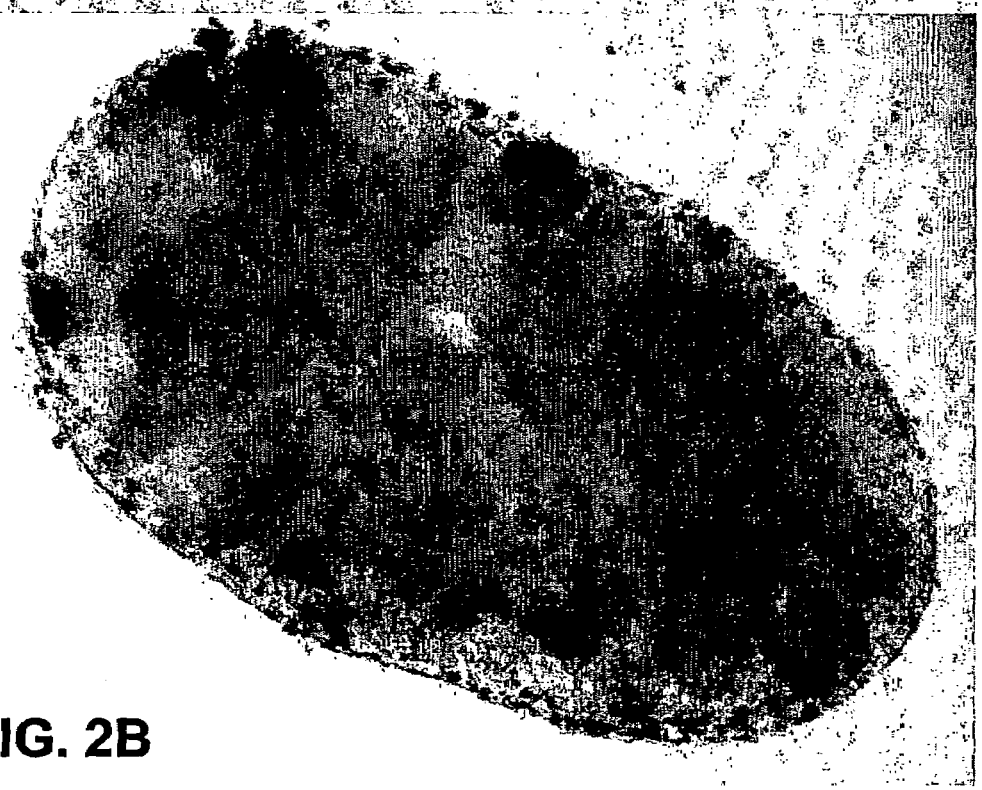

As shown in FIG. 2A-2B, HARV cultures of hepatocyte spheroids produce even larger spheroid aggregates with high viability. The inventors examined the relative sizes of spheroids cultured in HARVs versus those cultured in Petri dishes. From 50 random measurements, the average HARV spheroids were 2.3 times larger than dish spheroids. Only a small number of peripheral cells are non-viable, as shown in FIG. 2A-2B by their uptake of trypan blue stain (seen as black spots in these photos). Also visible under the microscope is tan to brown pigmentation in the cells (seen here as dark gray patches), presumably reflecting the presence of the bile pigment bilirubin. In the present inventors' experience, such pigmentation is correlated with spheroid viability. Transmission electron micrographs of cultures according to this invention show characteristics of hepatocytes that are seen in vivo.

Figure 3:
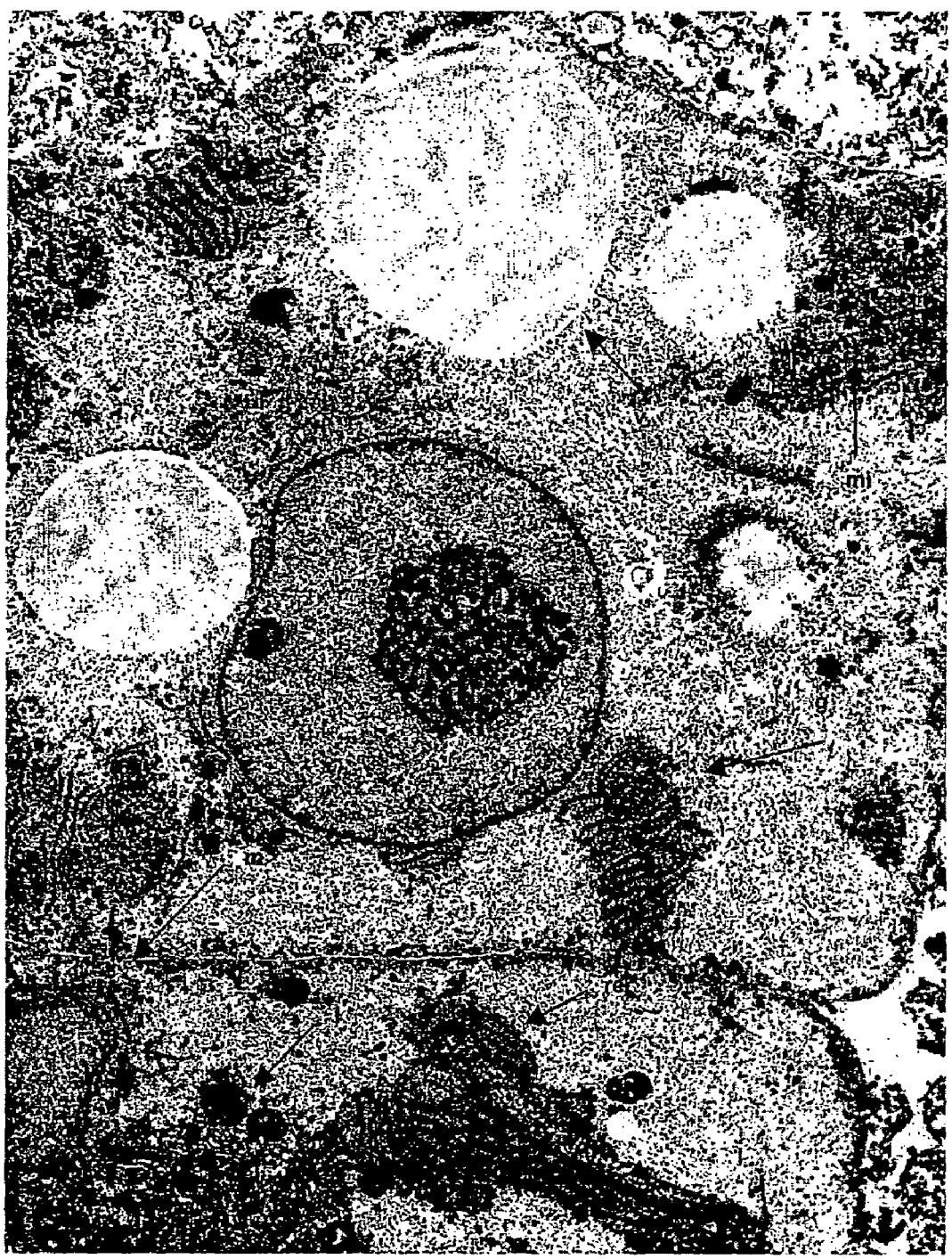
FIG. 3 shows a transmission electron micrograph (TEM) of rat hepatocytes from HARV culture showing numerous rough endoplasmic reticulum (rer); mitochondria (mi); lysosomes (l); Golgi apparatus (g); membrane junctions (m) with interdigitation of the membranes, and storage vesicles (v) that may be lipid droplets.

In particular, FIG. 3 shows copious rough endoplasmic reticulum, mitochondria, membrane junctions with interdigitations, lysosomes, Golgi apparatus, and storage vesicles (possibly lipid droplets). In other micrographs (not shown here), structures resembling bile canaliculi with luminal microvilli were observed.

EXAMPLE II

Long-Term Maintenance of Hepatocytes

FIG. 2 shows evidence of the capability of the present bioreactor and culture system to maintain hepatocyte viability for several weeks. Hepatocyte spheroids have been viably maintained, with activity of liver enzymes preserved, for over one month. This distinguishes the present invention from all other in vitro systems for simulating metabolism of a live mammal with an intact liver.

The first example of preservation of enzyme activity is shown in Table 1. Here, the activity of the cytochrome P450 enzyme 2B1/2 has been measured via the Pentoxyresorufin O-dealkylation (PROD) assay on disrupted and homogenized rat hepatocytes cultured in a HARV, as dish spheroids (SP), as monolayers (ML), and compared to freshly isolated cell suspensions (FS).

Freshly isolated rat liver cells exhibited a PROD activity of approximately 50 pmol/mg protein. Cells from this same isolation were maintained as monolayer, dish spheroid, and HARV spheroid cultures for many days and the PROD activity was measured periodically on small cell samples from these cultures. For monolayers and dish spheroids, this activity diminishes after the first day. In HARV culture, by contrast, PROD activity is maintained and even increases over a period of 39 days. Table 1 also shows the maintenance of testosterone 16β-hydroxylation, another CYP 2B1/2 activity, by HARV cultures over a period of 16 days.

In another example of preservation of enzyme activity, human hepatocytes were maintained in the HARV for 30 days and then "challenged" with a dose of 100 μM phenacetin. Within 6 hours of dosing, the metabolites acetaminophen and acetaminophen sulfate were measured at concentrations of approximately 250 and 50 nmoles per mg protein, respectively.

TABLE 1

| Day | FS | ML | SP | HARV |
|---|---|---|---|---|
| PROD activity (pmol/mg protein) | | | | |
| 0 | 48.6 | N/A | N/A | N/A |
| 1 | N/A | 11.4 | 25.0 | 25.0 |
| 4 | N/A | 0.0 | 1.9 | 25.3 |
| 7 | N/A | 0.15 | 0.0 | 31.6 |
| 16 | N/A | nd | nd | 53.5 |
| 39 | N/A | nd | nd | 61.1 |
| TST 16β-OH activity (pmol/mg protein) | | | | |
| 0 | 590 | N/A | N/A | N/A |
| 1 | N/A | 300 | 300 | nd |
| 4 | N/A | 80 | 0 | 190 |
| 7 | N/A | 180 | 0 | 350 |
| 16 | N/A | Nd | nd | 840 |

N/A = Not applicable
nd = not determined

EXAMPLE III

Whole-Cell Drug Metabolism

It is well known in the art that many of the liver-specific enzyme functions disappear following cultivation of hepatocytes in vitro. The present invention provides an important improvement over the prior art. Table 2 summarizes the metabolism of a variety of drug substrates tested on viable whole liver cells (rat and human hepatocyte cultures from HARV, spheroids cultured in Petri dishes (SP), and freshly isolated cell suspensions (FS)) using the present bioreactor system. Activity of multiple Cytochrome P450 (CYP) and Phase II conjugation enzymes was examined. Substrates were added at a concentration of 100 μM, with the exception of tolbutamide (1 mM), and 7-Hydroxycoumarin (10 μM). Activity is measured on whole live cells in culture and analyzed by HPLC of the culture medium.

TABLE 2

| | | | nmoles/mg protein/24 hr | | | | |
|---|---|---|---|---|---|---|---|
| Substrate | Metabolites measured | Enzyme | FS | 1-day SP | 7-day SP | 1-day HARV | 7-day HARV |
| Tolbutamide | 4-OH-tolbutamide | 2B;2C | 4 | 50 | 18 | 14 | 31 |
| Warfarin | 4-OH-warfarin | 3A | 2.3 | 43 | 13 | 15 | 2.4 |
| | 6-OH-warfarin | 1A;2C | 0.44 | 0.0 | 2.5 | 0.05 | 1.1 |
| | 7-OH-warfarin | 2C | 0.05 | 0.4 | 0.77 | 0.0 | 0.45 |
| Chlorzoxazone | 6-OH-chlorzoxazone | 2E;1A | 4.7 | 2.7 | 2.9 | 1.3 | 1.1 |
| Dextromethorphan | dextrorphan | 2D | 5.6 | 1.5 | 0.85 | 0.63 | 0.33 |
| | 3-methoxy-morphinan | 3A | 5.5 | 7.9 | 2.7 | 1.7 | 9.2 |
| | 3-hydroxy-morphinan | 2D;3A | 0.99 | 1.6 | 0.3 | 0.61 | 1.0 |

TABLE 2-continued

| | | | nmoles/mg protein/24 hr | | | |
|---|---|---|---|---|---|---|
| Substrate | Metabolites measured | Enzyme | FS | 1-day SP | 7-day SP | 1-day HARV | 7-day HARV |
| 7-Hydroxycoumarin (7-HC) | 7-HC sulfate | GST* | 0.41 | 2.3 | 1.8 | 5.8 | 5.0 |
| | 7-HC glucuronide | UDP-GT* | 2.1 | 2.1 | 8.3 | 11 | 30 |
| Midazolam | 1-OH-midazolam | 3A | 10 | 7.3 | 8.6 | 1.4 | 4.5 |
| | 4-OH-midazolam | 3A | 33 | 10 | 15 | 2.6 | 17 |
| Acetaminophen (a) | a. sulfate | GST | 7.5 | 250 | 130 | 4.2 | 30 |
| | a. glucuronide | UDP-GT | 0.87 | 41 | 52 | 11 | 33 |
| Phenacetin | Acetaminophen | 1A | 0.37 | 9.2 | 54 | 11 | 50 |
| | a. sulfate | GST | 6.0 | 34 | 17 | 10 | 6.4 |
| | a. glucuronide | UDP-GT | 0.0 | 0.0 | 0.0 | 0.0 | 0.0 |
| Phenacetin[†] | Acetaminophen | 1A | nd | 200 | 21 | 44 | 70 |

*Phase II metabolism enzymes: GST = glutathione-S-transferase; UDP-GT = uridine diphosphate glucuronyltransferase
[†]Second group of phenacetin data applies to metabolism by human hepatocytes. Note that in a separate experiment with human hepatocytes in the HARV, a secondary metabolite, acetaminophen sulfate was detected.

This drug metabolism is shown in comparison to that measured for hepatocyte spheroids in Petri dishes and freshly isolated hepatocytes in suspension. Table 2 shows the metabolites thus far identified by HPLC assay and the amount produced per day per milligram of cellular protein. These metabolites are the result of action by CYP enzymes, with several distinct Phase I oxidation activities measured, and/or conjugation by Phase II enzymes.

With reference to Table 2, each "suspension culture" consisted of freshly isolated liver cells added to "adherent" 24-well plates to form partially attached cell monolayers over the 24 hour period during which metabolism was measured. Spheroid aggregates of fresh cells were formed in mixed Petri dishes. At the end of this formation period, spheroids were considered "fully developed" and were designated "1-day old." At this time, spheroids were either combined at a higher concentration in a fresh Petri dish or were transferred to a HARV for further culture and assay of metabolite production. Separate and parallel cultures of spheroids in dishes and spheroids in HARVs were maintained and fed for 7 days prior to the final assay of drug metabolite production.

In each study represented in Table 2, hepatocytes were "challenged" by adding a drug substrate to the cultures. Metabolites were measured after 24 hours incubation. Comparisons were made between (1) freshly isolated cells; (2) 1-day and 7-day-old spheroids in dishes; and (3) 1-day and 7-day-old spheroids in HARVs.

In more than 60% of the cases for HARV spheroids, 7-day-old cultures generated more metabolite than did 1-day-old cultures. This was true in only 40% of cases for spheroids cultured in Petri dishes. This pattern is not surprising given the increase over time in PROD and testosterone 16-β-hydroxylation activities documented in Example II for the hepatocyte bioreactor cultures. Like the data in Example I, CYP 2B activity is seen again here as well preserved in HARV cultures.

There was an indication of reduced recovery of some substrate and metabolite compounds from the HARVs, compared with the other culture modes. This could potentially be due to the following: (1) reduced availability through adsorption to the bioreactor surfaces or diffusion limitations due to the larger size of spheroids in the HARV; (2) inadequate recovery of the intracellular fraction of the drug; (3) loss of cellular protein on harvest or feeding. Regardless, the present system exhibits consistent and continuous production of metabolites from many important drug substrates, as shown. Coupled with the greatly enhanced longevity of these HARV cultures, the present hepatocyte bioreactor system promises to be an excellent tool for drug metabolism studies.

EXAMPLE IV

Protein and Urea Production

Figure 4:
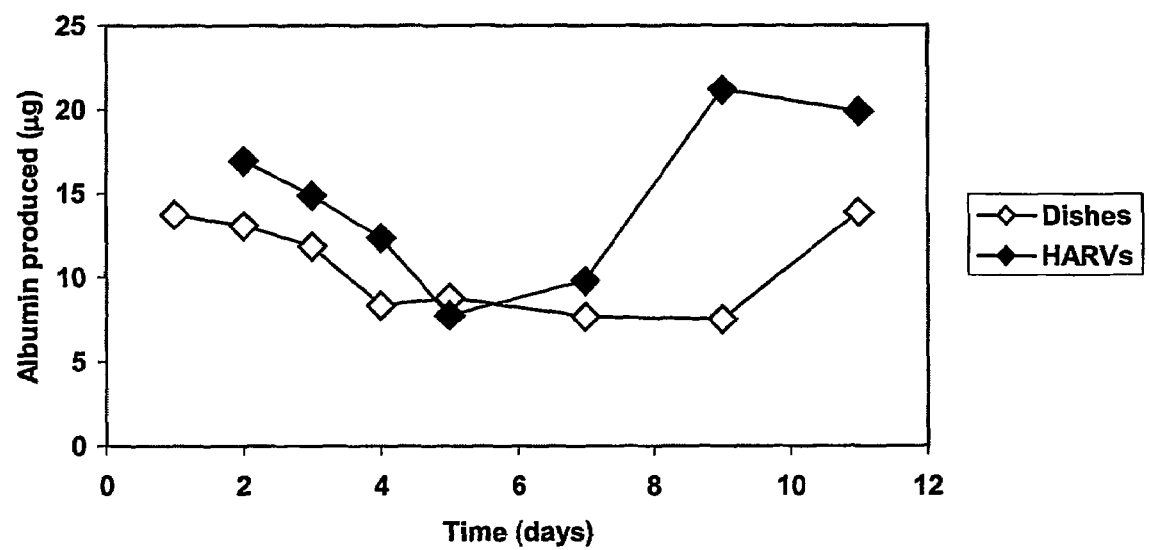
FIG. 4 is a graph showing albumin production over time by spheroids cultured in Petri dishes versus spheroids cultured in HARVs.

The production of albumin, an important plasma protein synthesized in the liver, was measured in HARV cultures compared to spheroids in Petri dishes (FIG. 4) over the course of several days. Albumin production was, on average, 30% higher in the HARV cultures and was maintained for at least 11 days.

The inventors measured endogenous urea production by rat hepatocytes as spheroid cultures in HARVs, spheroids in dishes, and monolayers. The average production rates over 11 days in culture were:

| | |
|---|---|
| Monolayer | 35 ± 11 µg urea/mg protein/day |
| Dish spheroids | 41 ± 13 µg urea/mg protein/day |
| HARV spheroids | 59 ± 6 µg urea/mg protein/day |

The formation of urea from an exogenous source of ammonia was measured using porcine hepatocytes in a perfused RWV, a vessel related to, although different from, the HARV. Approximately 80 µmoles of urea was formed overnight in culture from 170 µmoles of $NH_4Cl$ added.

EXAMPLE V

Propagation of Hepatitis C Virus and Drug Testing

To test the ability of the present hepatocyte bioreactor system to support infection and propagation of Hepatitis C virus, a culture of primary hepatocytes is first established in HARV bioreactors. Hepatitis C virus is introduced in the form of infectious serum (from an HCV-infected subject).

The establishment and progress of HCV infection is monitored with regular sampling of cells and/or medium from the bioreactor. A successful outcome is demonstrated by (i) presence of HCV negative-strand RNA; (ii) long-term production of HCV positive-strand RNA; and (iii) transmission of infection to cells of a fresh hepatocyte culture.

Quantification of viremia is accomplished by detecting viral core antigen by fluorescent enzyme immunoassay (Tanaka, T et al., 1995, *J. Hepatology* 23:742-745) by measuring HCV RNA using the Amplicor HCV Monitor test (Roche Molecular Systems, Pleasanton, Calif.) or the Quantiplex HCV RNA 2.0 assay (bDNA; Chiron, Emeryville, Calif.).

Total RNA is purified using the RNAqueous® kit (Ambion, Austin, Tex. or High Pure RNA Isolation kit (Boehringer Mannheim, Germany).

Production of the negative RNA strand is measured by the method of tagged RT-PCR amplification (Lanford, RE et al., 1994, *Virology* 202: 606-614), followed by Southern blot hybridization.

Human infectious serum and human hepatocytes are obtained from reliable sources, with donor consent.

A form of positive control is the passage of viral infection from the supernatant of one bioreactor to a naïve culture. As a negative control, normal non-infectious human serum is added to identical bioreactor cultures.

The following parameters are varied in these studies: (1) initial number of hepatocytes in the bioreactor: between $5 \times 10^6$ and $5 \times 10^8$ cells; (2) hepatocyte source: primary or cryopreserved hepatocytes from human adults or fetuses or from chimpanzees; (3) age of hepatocyte culture (e.g., 1-10 days in bioreactor prior to infection); (4) HCV titer of infectious serum, between about $5 \times 10^6$ and about $10^9$ equivalents/mL; and (5) other properties of the serum including titers of anti-HCV antibodies that are specific for HCV proteins.

Bioreactor cultures will be started, initially using the preferred cell concentration of $5 \times 10^6$ cells/mL. Hepatitis C virus will be seeded into HARV cultures between days 1 to 10, at titers of 0.25 to $2.5 \times 10^5$ copies/mL (Rumin, S. et al., 1999, *J. Gen. Virol.* 80:3007-3018; Fournier, C. et al., 1998, *J. Gen. Virol.* 79:2367-2374). Infection is sustained, along with the hepatocyte culture, for an extended period, ranging between about 7 and about 30 days, to reach a titer of 0.5 to $5 \times 10^6$ copies/mL.

Proof that HCV was successfully propogated is obtained by measuring increased viral RNA content and by transmission of virus from an infected culture to a naïve HARV culture where it again propagates.

The ultimate test of successful production of competent infectious particles is by infection and Hepatitis C disease induction in a chimpanzee model using virus generated in the present bioreactor culture. Using culture supernatants that are positive by in vitro infectivity, quantities equivalent to $10^4$ to $10^{6.2}$ 50% chimpanzee infective doses ($CID_{50}$) will be administered i.v. to chimpanzees (Feinstone, S M et al., 1983, *Infect. Immun.* 41:816-821; Shimizu, Y K et al., 1990, *Proc. Nat. Acad. Sci.* 87:6441-6444). Clinical signs of acute hepatitis C will appear in 80% of the recipients within 6 to 15 weeks. These signs include elevated serum alanine aminotransferase levels, anti-HCV antibodies, serum viral RNA measurable by qualitative PCR, and/or ultrastructural changes seen on liver biopsy.

The foregoing Hepatitis C model is used to test the effect of a therapeutic candidate, whether small molecule, peptide or biological macromolecule. Different concentrations of the candidate in parallel with a negative control, are added to cultures established under selected conditions determined as above. The cultures are monitored for a decrease in viral load or a static effect on viral growth in comparison with the negative control. As a positive control, an agent or regimen with known anti-HCV activity can be run concurrently, for example, the nucleoside analogue Ribavirin (e.g., Virazole®, Rebetol®), interferon-α, preferably interferon α-2b (e.g., Roferon-A®, Intron-A®) (which is the FDA-approved standard treatment of HCV infection), or the combination of Ribavirin and interferon-α.

The present bioreactor system may be used as a model for infectious diseases other than Hepatitis C, wherein the pathogenic organism replicates in hepatocytes, with minor modifications to the protocol that are tailored to the pathogenic organism of interest.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

What is claimed is:

1. A method for cultivation of mammalian hepatocytes in a viable functional state, which comprises the steps of:
   (a) culturing a single cell suspension of mammalian hepatocytes in a culture medium for a period of between about 12 and about 168 hours in a culture vessel having a flat surface under conditions that permit aggregation of hepatocytes into spheroids which comprise viable hepatocytes;
   (b) transferring said spheroids into a rotating wall vessel (RVW) culture chamber where said spheroids remain substantially in suspension during subsequent culture with rotation; and
   (c) incubating said suspended spheroids under conditions of vessel rotation such that said spheroids remain substantially in suspension;
   wherein suspended spheroids remain viable and capable of:
   (i) producing and secreting normal hepatocyte products; and
   (ii) metabolizing drugs or toxins via enzymes of the cytochrome P450 system, which drugs or toxins are ones that are normally metabolized by hepatocytes in vivo for more than 30 days.

2. The method of claim 1 wherein the RWV is a High Aspect Ratio Vessel (HARV).

3. The method of claim 1 wherein the culturing of step (a) is for a time of between about 24 and about 72 hours.

4. The method of claim 1 wherein the culture vessel of step (a) is a plastic petri dish.

5. The method of claim 1 wherein the culture medium is selected from the group consisting of Waymouth MB 752, Williams' Medium E, Eagle's MEM; Dulbecco's MEM/Ham's F12, RPMI 1640, and Leibovitz L-15 medium.

6. The method of claim 1 wherein the culture medium is supplemented with serum.

7. The method of claim 1 wherein the culture medium is supplemented with:
   (a) one or more growth factors, and/or
   (b) one or more peptide hormones, and/or
   (c) one or more glucocorticoids
   which growth factors, hormones and glucocorticoids promote the viability and metabolic activity of the hepatocytes.

8. The method of claim 7 wherein said growth factors comprise epidermal growth factor, said hormones comprise insulin or glucagon; and said glucocorticoids comprise dexamethasone or hydrocortisone.

9. The method of claim 1 wherein said hepatocytes are primate hepatocytes.

10. The method of claim 9 wherein said primate hepatocytes are human hepatocytes.

11. A method for cultivation of mammalian hepatocytes in a viable functional state, which comprises inoculating a High Aspect Ratio Vessel (HARV) with pre-aggregated hepatocytes or nascent hepatocyte spheroids, in a culture medium and incubating said hepatocytes and under conditions wherein hepatocytes are viable and metabolically active for a period of at least about 4 days:

wherein said hepatocytes remain viable and capable of:
(i) producing and secreting normal hepatocyte products; and
(ii) metabolizing drugs or toxins via enzymes of the cytochrome P450 system, which drugs or toxins are ones that are normally metabolized by hepatocytes in vivo for more than 30 days.

* * * * *